United States Patent [19]

Moreton et al.

[11] Patent Number: 4,778,630

[45] Date of Patent: Oct. 18, 1988

[54] MICROBIAL DESATURASE ENZYME INHIBITORS AND THEIR USE IN A METHOD OF PRODUCING LIPIDS

[75] Inventors: Rodney S. Moreton, Salisbury; David M. Clode, Reading, both of England

[73] Assignee: Cadbury Schweppes Plc, London, England

[21] Appl. No.: 710,963

[22] Filed: Mar. 12, 1985

[30] Foreign Application Priority Data

Mar. 20, 1984 [GB] United Kingdom ............... 8407195

[51] Int. Cl.$^4$ .............................................. C11C 3/02
[52] U.S. Cl. ..................... 260/410.9 R; 260/405.5; 560/124; 562/406
[58] Field of Search .............. 560/124; 260/410.9, 260/405.5; 562/406

[56] References Cited

U.S. PATENT DOCUMENTS 3,465,008  9/1969  Mills ................................. 560/124
3,654,324  4/1972  Gensler ............................. 560/124
3,699,146  10/1972 Gensler ............................. 560/124

FOREIGN PATENT DOCUMENTS 2091286  7/1982  United Kingdom .

OTHER PUBLICATIONS

Forgerty, et al., *Lipids*, 7:355–338, 1972.
Pawlowski et al., *J. Org. Chem.* 37:3245–3248, 1972.

Primary Examiner—Paul J. Killos
Attorney, Agent, or Firm—Holman & Stern

[57] ABSTRACT

The invention provides novel cyclopropene fatty acid compounds of formula (I)

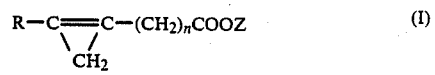

(I)

wherein R is a straight chain aliphatic group of 1 to 6 carbon atoms, n is an integer of from 10 to 15; Z is a hydrogen atom, or an alkyl group of 1 to 6 carbon atoms. Also provided is a method of producing lipids comprising cultivating a suitable lipid accumulating microorganism in a growth medium containing at least one cyclopropene fatty acid or its derivative of general formula

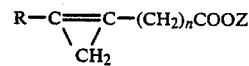

wherein n is an integer greater than 8 and Z and R are as defined above, the CPFA acting as a desaturase inhibitor. At least one CPFA desaturase inhibitor may be introduced into a nitrogen limited growth medium for microorganisms in an amount such that when a suitable microorganism is cultivated in such a medium, one or more desaturase enzymes are inhibited so that higher levels of saturated or less saturated lipids may be produced which may be used in fat compositions as cocoa butter equivalents.

9 Claims, No Drawings

MICROBIAL DESATURASE ENZYME INHIBITORS AND THEIR USE IN A METHOD OF PRODUCING LIPIDS

The present invention relates to cyclopropene fatty acid compounds, a method of manufacture of such compounds and a method of producing lipids containing saturated fatty acid esters using microorganisms and cyclopropene fatty acid compounds as desaturase enzyme inhibitors.

GB No. 2091286 A, GB No. 2091285 A, GB No. 1501355 and GB No. 1555000 have suggested that the type of lipid produced by lipid accumulating microorganisms can be modified by the inclusion of fatty acid derivatives in the culture medium to produce a lipid more like cocoa butter, which means in practice increasing the stearic acid content to around 35% of the triglyceride fatty acid fraction.

Most microbial fats contain too much linoleic (18:2) acid to be useful cocoa butter equivalents (CBE). Ideally a CBE should contain less than 4% linoleic acid and the content of linolenic (18:3) acid should be less than 0.5%.

The above mentioned GB 2091286 A has suggested that by using emulsions of fatty acids having 10 to 20 carbon atoms, and by use of a desaturase inhibitor, such as the naturally occurring cyclopropene fatty acid (CPFA) sterculic acid, or oils containing these acids such as cottonseed oil, a fat can be produced which is very similar to cocoa butter. However, it would be preferable to use a cheaper growth medium containing no fatty acids or their derivatives, based on a readily available carbohydrate such as glucose or sucrose. When grown on such carbohydrate based nitrogen limited media, lipid accumulating yeasts produce a lipid too low in stearic acid (18:0) and too high in oleic acid (18:1) and linoleic acid (18:2) [cocoa butter has a typical composition of 26% palmitic acid (16:0), 36% stearic acid (18:0), 33% oleic acid (18:1) and 3% linoleic acid (18;2)]. The ratio of stearic to oleic acid may be altered by incorporating stearic acid or its derivatives into the growth medium, or by addition of a desaturase inhibitor such as sterculic acid as disclosed in the above mentioned GB No. 2091286 and GB No. 2091285.

It is believed that the desaturase enzyme inhibitor serves to minimise the effect of intracellular desaturase and so prevents desaturation of the stearic acid. Thus the use of desaturase enzyme inhibitor results in increased stearic acid levels found in the resulting triglycerides.

However, the linoleic acid (18:2) content is still too high with most lipid accumulating organisms. The desired level for a good CBE is less than 4 wt %. The desaturase inhibitors such as sterculic acid do not directly reduce the content of linoleic acid in these organisms.

The naturally occurring CPFA's sterculic acid and malvalic acid, are 18 carbon and 17 carbon fatty acids respectively, with the cyclopropene group in the Δ9 position relative to the carboxyl group.

GB No. 2091286 refers broadly to desaturase enzyme, but it has been found that there are in fact three different desaturase enzymes responsible for the desaturation of the 18 carbon family of fatty acids. The first desaturation, to which they are referring directly in the above mentioned patent, is the one which converts stearic acid to oleic acid, by insertion of a double bond in the Δ9 position. Similarly a Δ12 desaturase is responsible for the insertion of a second double bond in the Δ12 position to convert oleic acid (18:1) to linoleic acid (18:2), and likewise a Δ15 desaturase inserts a third double bond in the Δ15 position to convert linoleic acid to linolenic acid (18:3).

The two naturally occurring CPFA's, sterculic acid and malvalic acid, which have the cyclopropene group in the Δ9 position, only directly inhibit the Δ9 desaturase, not the Δ12 or Δ15 desaturase enzymes.

It is one object of this invention to obviate or mitigate the above mentioned problems.

In one aspect of the present invention there is provided a cyclopropene fatty acid compound of formula (I)

wherein R is a straight chain aliphatic group of 1 to 6 carbon atoms; n is an integer of from 10 to 15; Z is a hydrogen atom, or an alkyl group of 1 to 6 carbon atoms.

In the preferred case, R is a straight chain alkyl group of 1 to 5 carbon atoms, n is an integer from 10 to 14 and Z is either a hydrogen atom or a methyl group.

In another aspect of the invention there is provided a method of producing a compound of formula (I) as defined above comprising the steps of reacting a primary alkyne with an halogenated carboxylic acid to form an alkyne acid, esterifying the acid thus formed, converting the alkynilic bond to a 1,2,3 tri-substituted cyclopropene group, and then removing the 3 substituent and, optionally, the ester group if present to leave a CPFA or one of its derivatives.

It is not essential to esterify and the CPFA may be used in either its ester or free acid form.

Reaction Scheme

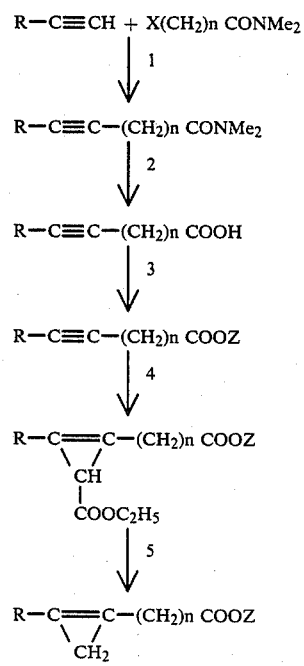

A preferred method of production of CPFA compounds is to use the reaction scheme described above wherein the halogenated acid is a bromoacid and step 1 is achieved by using a strong base such as sodamide; the hydrolysis of the amide (step 2) is achieved using a base such as sodium hydroxide; the esterification of step 3 is achieved by using concentrated sulphuric acid and the appropriate alcohol preferably methanol; cyclisation step (4) is achieved using ethyl diazoacetate and the final step (5) is achieved using fluorosulfonic acid followed by sodium borohydride. This method is outlined below:

Step 1 is normally carried out at −70° C. to −33° C.; for 360 min. to 900 min.

Step 2 is normally carried out at 50° C. to 150° C.; for 360 min to 480 min.

Step 3 is normally carried out at 50° C. to 150° C.; for 30 min to 120 min.

Step 4 is normally carried out at 100° C. to 150° C.; for 60 min to 240 min.

Step 5 is normally carried out at 10° C. to 30° C.; for 30 min to 120 min (fluorosulphonic acid addition); −70° C. to −30° C.; for 30 min. to 120 min. (sodium borohydride addition).

Certain CPFA's of the present invention may be used as desaturase enzyme inhibitors. The use of naturally occurring Δ9 desaturase inhibitors has been previously proposed, but we have found that these compounds have no direct effect on the Δ12 and Δ15 desaturase enzymes, and the residual levels of 18:2 are too high for a CBE. CPFA's of the present invention may be added to microorganism growth media to act as Δ12 and Δ15 desaturase inhibitors respectively and consequently reduce the amount of unsaturated fatty acids produced, particularly oleic, linoleic and linolenic acids, and increase the amount of saturated acid produced, particularly stearic acid.

To act as a Δ12 desaturase inhibitor, the compound of formula (I) is preferably Δ12 CPFA (i.e. n is 10). However, Δ11 and Δ13 CPFA's (where n is 9 and 11 respectively) may also act as Δ12 desaturase inhibitors.

Likewise, a Δ15 desaturase inhibitor may be a Δ14, Δ15 or Δ16 CPFA of the formula (I) (where n is 12, 13 or 14, respectively).

It is generally preferred that the straight chain portion of the CPFA is 17 or 18 carbon atoms long.

In another aspect of the present invention there is provided a method of producing lipids comprising cultivating a suitable lipid accumulating microorganism in a growth medium containing at least one cyclopropene fatty acid or its derivative of general formula

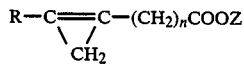

wherein n is an integer greater than 8 and Z and R are as defined above, the CPFA acting as a desaturase inhibitor.

Typically said at least one CPFA desaturase inhibitor is introduced into a nitrogen limited growth medium for microorganisms in an amount such that when a suitable microorganism is cultivated in such a medium, one or more desaturase enzymes are inhibited so that higher levels of saturated or less saturated lipids may be produced. The cultivation conditions are dependent on the microorganism used. Typically cultivation is carried out at pH 3.0 to 7.0 and at 15°–30° C.

A preferred use of the above technique is in the production of fat compositions to be used as cocoa butter equivalents (CBE) using suitable lipid-accumulating microorganisms grown in a carbohydrate based nitrogen limited growth medium. It is envisaged that continuous cultures will be used in production of CBE's although any cultivation method may be used.

Δ15 desaturase inhibitors prevent the desaturation of the Δ15 bond and so only directly inhibit the formation of linolenic acid (18:3), Δ12 desaturase inhibitors likewise inhibit the formation of the Δ12 double bond and consequently only directly inhibit the formation of linoleic acid (18:2) and the known Δ9 desaturase inhibitors only directly inhibit the formation of the Δ9 double bond and so only directly prevent the formation of oleic acid (18:1). The combined effect of these three types of desaturase inhibitors is to inhibit the formation of unsaturated C-18 fatty acids and consequently the amount of stearic acid (18:0) produced is increased. Each type of desaturase inhibitor inhibits a complementary type of desaturase enzyme. Preferably Δ9, Δ12 and Δ15 desaturase inhibitors are present in the growth medium for the production of CBE's.

The CPFA desaturase inhibitors are typically incorporated into the culture medium at concentrations of 0.0125 to 4.0 μl/ml, the ratio of the individual inhibitors being adjusted to give the required amounts of saturated and unsaturated fatty acids. The amount of desaturase inhibitor used is dependent on the microorganism to be used.

A typical nitrogen limited carbohydrate based growth medium comprises: potassium dihydrogen orthophosphate at a concentration of 7.0 g/l, disodium hydrogen orthophosphate at a concentration of 2.0 g/l, magnesium sulphate at a concentration of 1.5 g/l, calcium chloride at a concentration of 0.1 g/l, iron (III) chloride at a concentration of 0.008 g/l, zinc sulphate at a concentration of 0.0001 g/l, yeast extract at a concentration of 1.5 g/l, a carbon source (glucose, sucrose, fructose, lactose, xylose, glycerol or similar) at a concentration of 30 g/l, and ammonium chloride at a concentration of 0.5 g/l or an organic nitrogen source (L glutamic acid, sodium glutamate, urea or similar) at a concentration chosen to give the same C:N ratio as with the ammonium chloride (or a similar inorganic nitrogen source), at a pH of 5.5 with organic sources of nitrogen being preferable to inorganic sources when being used for lipid production.

Lipid-accumulating yeasts to be used in the present invention are, for example, selected from *Rhodosporidium toruloides* IFO 0559, *Candida* sp. NCYC 911 and *Apiotrichum curvatum* ATCC 20509. *Trichosporon* sp. ATCC 20505, *Rhodotorula gracilis* ATCC 10788, *Rhodotorula graminis* NCYC 502 and CBS 3043 may also be used. However, we have found that the following yeasts may provide problems when used in the present invention: *Saccharomyces cerevisiae* NCYC 33, *Rhodosporidium toruloides* IFO 113 and the following members of the genus Lipomyces; *L. lipofer* NCYC 982, *L. starkeyi* NCYC 692, CBS 6142, CBS 6, CBS 6047, CBS 0678, CBS 6132 and CBS 1807. In some of these cases CPFA's appear to be toxic to the yeast. Thus, one of the criteria for a suitable microorganism is that its cultivation must be possible in the presence of the chosen desaturase inhibitor. Simple screening tests may be used to establish other microorganisms which are suitable for use in the present invention.

Examples

EXAMPLE 1

Synthesis of 11-(2-pentylcyclopropene-1-yl) undecanoic acid methyl ester.

0.24 Mol of 1-heptyne is stirred with 0.15 mol of N,N-dimethyl-11-bromoundecanamide in liquid ammonia in the presence of 0.3 mol of sodamide for 900 minutes at $-33°$.

The $C_{18}$-alkyne amide produced above is refluxed with 5M sodium hydroxide solution in ethanol for 480 minutes.

The resulting alkyne acid is refluxed with methanol containing 4% concentrated sulphuric acid for 60 minutes.

The methyl ester (20 mmol) thus obtained is stirred with 30 mmol of ethyl diazoacetate for 180 minutes at 135° C.

The resulting cyclopropene (5.25 mmol) is stirred with 43.7 mmol of fluorosulphonic acid for 60 minutes at room temperature, followed by reduction with 26.3 mmol of sodium borohydride in methanol saturated with sodium hydroxide for 30 minutes at $-50°$ C.

This gives a 12 cyclopropene fatty acid (methyl ester) characterised by the following: (a) Positive Halphen test (b) Peaks at 1875 and 1010 $cm^{-1}$ (cyclopropene) in the infra red spectrum (c) The following signals in the $^1$H-n.m.r. spectrum, 0.77 (s, 2 H cyclopropenyl $CH_2$), 0.90 (t, 3H, J 6.0Hz, terminal $CH_3$), 1.1–1.8 (m,22H, internal $CH_2$), 2.18–2.50 (m,6H, alpha to cyclopropenyl and $—CO_2CH_3$, and 3.67 (s,3H, methyl ester $CH_3$) (d) The following signals in the $^{13}$C-n.m.r. spectrum, 7.42 (cyclopropenyl $CH_2$), 14.03 (terminal $CH_3$), 51.30 (methyl ester $CH_3$), 109.43 (cyclopropenyl c=c) and 174.20 ppm (carboxylic $CO_2$).

EXAMPLE 2

A nitrogen limited, carbohydrate based growth medium of the above mentioned type was made up, sterilized and 50 ml placed in sterile shake flasks;

To the shake flasks were added known quantities of sterculia oil and then the Δ12 CPFA produced as described in Example 1, and the flasks were then inoculated with cultures of *Rhodosporidium toruloides* IFO 0559, *Candida* sp. NCYC 911, or *Apiotrichum curvatum* ATCC 20509 and incubated at 30° C. for 4 days in an orbital incubator at 250 rpm.

The cells were then harvested by centrifugation, freeze dried and extracted with chloroform/methanol by Bligh & Dyers modification of the method of Folch et al. The extracted lipid was methylated and analysed by gas chromatography. The results obtained are displayed in the Table 1 below.

TABLE I

Composition of extracted yeast lipids after growth with sterculia oil and Δ12 CPFA

| Organism | Sterculia oil, ml/l | Δ12 CPFA ml/l | Biomass g/l | Lipid % w/w | Fatty acid composition % w/w | | | | |
|---|---|---|---|---|---|---|---|---|---|
| | | | | | 16:0 | 18:0 | 18:1 | 18:2 | 18:3 |
| *Rhodosporidium toruloides* IFO 0559 | — | — | 7.13 | 23.5 | 27.7 | 7.3 | 38.9 | 17.5 | 4.6 |
| *Rhodosporidium toruloides* IFO 0559 | 0.3 | — | 7.55 | 22.51 | 14.8 | 48.3 | 18.5 | 9.1 | 3.7 |
| *Rhodosporidium toruloides* IFO 0559 | — | 0.4 | 7.80 | 19.73 | 35.9 | 8.3 | 44.7 | 1.8 | — |
| *Rhodosporidium toruloides* IFO 0559 | 0.3 | 0.3 | 7.95 | 34.21 | 19.5 | 46.8 | 21.8 | 4.7 | 1.5 |
| *Candida sp* NCYC 911 | — | — | 8.72 | 31.21 | 28.5 | 13.2 | 37.6 | 13.0 | 0.8 |
| *Candida sp* NCYC 911 | 0.1 | — | 6.47 | 28.65 | 24.6 | 50.1 | 8.5 | 3.9 | 0.7 |
| *Candida sp* NCYC 911 | 0.1 | 0.1 | 7.83 | 28.63 | 42.2 | 35.5 | 8.0 | 0.5 | 0.4 |
| *Apiotrichum curvatum* ATCC 20509 | — | — | 6.71 | 48.7 | 31.7 | 15.5 | 43.7 | 8.6 | 0.3 |
| *Apiotrichum curvatum* ATCC 20509 | 0.1 | — | 8.57 | 55.16 | 26.7 | 26.4 | 35.5 | 7.8 | 0.6 |
| *Apiotrichum curvatum* ATCC 20509 | 0.4 | 4.0 | 7.96 | 52.34 | 41.1 | 25.2 | 28.1 | 0.4 | — |

The following Tables 2 and 3 show the effects of using various amounts of sterculia oil and the above-described CPFA on the fatty acid compositions of *Rhodosporidium toruloides* IFO 0559 and *Candida* sp 107, NCYC 911, respectively.

TABLE 2

EFFECT OF STERCULIA OIL ON FATTY ACID COMPOSITION OF *RHODOSPORIDIUM TORULOIDES*, IFO 0559

| Sterculia oil ml $l^{-1}$ | Δ12 CPFA ml $l^{-1}$ | Biomass g $l^{-1}$ | Lipid g $l^{-1}$ | Lipid % w/w | Fatty acid composition % w/w | | | | | | Ratio 18:0/18:1 | ΔU |
|---|---|---|---|---|---|---|---|---|---|---|---|---|
| | | | | | 16:0 | 16:1 | 18:0 | 18:1 | 18:2 | 18:3 | | |
| 0 | 0 | 12.33 | 3.70 | 30.05 | 16.2 | 1.0 | 3.5 | 42.0 | 28.5 | 5.0 | 0.1 | 3.8 |
| 0.04 | 0.02160 | 8.48 | 2.65 | 29.97 | 15.1 | 1.0 | 17.1 | 19.0 | 17.0 | 8.8 | 0.9 | 1.4 |
| 0.10 | 0.0540 | 10.14 | 3.38 | 32.57 | 21.5 | 1.0 | 22.0 | 24.1 | 17.9 | 8.0 | 0.9 | 1.2 |

TABLE 2-continued
EFFECT OF STERCULIA OIL ON FATTY ACID COMPOSITION OF *RHODOSPORIDIUM TORULOIDES*, IFO 0559

| Sterculia oil ml l$^{-1}$ | Δ12 CPFA ml l$^{-1}$ | Biomass g l$^{-1}$ | Lipid g l$^{-1}$ | Lipid % w/w | \multicolumn{6}{c}{Fatty acid composition % w/w} | Ratio 18:0/18:1 | ΔU |
|---|---|---|---|---|---|---|---|---|---|---|---|---|
| | | | | | 16:0 | 16:1 | 18:0 | 18:1 | 18:2 | 18:3 | | |
| 0.20 | 0.1080 | 10.13 | 3.56 | 33.82 | 15.1 | 1.0 | 31.5 | 22.6 | 14.6 | 6.7 | 1.4 | 0.9 |
| 0.40 | 0.2160 | 8.81 | 2.58 | 28.95 | 17.3 | 1.0 | 31.7 | 17.1 | 17.0 | 9.2 | 1.9 | 0.9 |
| 0.80 | 0.4320 | 10.80 | 3.82 | 35.39 | 17.6 | 1.0 | 31.0 | 24.1 | 15.8 | 6.2 | 1.3 | 1.0 |
| 1.20 | 0.6480 | 10.45 | 2.27 | 22.53 | 17.0 | 1.0 | 30.7 | 24.1 | 15.9 | 4.8 | 1.3 | 0.9 |
| 1.60 | 0.8640 | 11.08 | 2.86 | 25.95 | 15.1 | 1.0 | 37.8 | 19.5 | 16.2 | 6.4 | 1.9 | 0.8 |
| 2.00 | 1.0800 | 10.29 | 3.29 | 31.94 | 12.9 | 1.0 | 40.9 | 18.0 | 14.9 | 6.1 | 2.3 | 0.7 |
| 4.00 | 2.1600 | 11.63 | 3.57 | 30.31 | 14.5 | 1.0 | 35.3 | 19.6 | 16.1 | 6.2 | 1.8 | 0.8 |

Degree of unsaturation $\Delta U = \dfrac{(18:1 + 18:2 + 18:3)}{(18:0 + 16:0)}$

TABLE 3
EFFECT OF STERCULIA OIL ON FATTY ACID COMPOSITION OF CANDIDA SP. 107, NCYC 911

| Sterculia oil ml l$^{-1}$ | Δ12 CPFA ml l$^{-1}$ | Biomass g l$^{-1}$ | Lipid g l$^{-1}$ | Lipid % w/w | \multicolumn{6}{c}{Fatty acid composition % w/w} | Ratio 18:0/18:1 | ΔU |
|---|---|---|---|---|---|---|---|---|---|---|---|---|
| | | | | | 16:0 | 16:1 | 18:0 | 18:1 | 18:2 | 18:3 | | |
| 0    | 0      | 9.90 | 3.05 | 30.85 | 27.7 | 2.5 | 5.2  | 32.9 | 27.2 | 1.0 | 0.2 | 1.8 |
| 0.04 | 0.0216 | 4.71 | 0.86 | 17.67 | 28.3 | 2.4 | 24.4 | 11.9 | 30.4 | 1.0 | 2.1 | 0.8 |
| 0.10 | 0.0540 | 5.25 | 1.19 | 21.29 | 29.3 | 1.0 | 28.5 | 9.8  | 25.0 | 1.0 | 2.9 | 0.6 |
| 0.20 | 0.1080 | 6.04 | 1.51 | 24.70 | 28.2 | 1.0 | 32.9 | 10.3 | 23.0 | 1.0 | 3.2 | 0.5 |
| 0.40 | 0.2160 | 6.70 | 1.82 | 26.76 | 28.7 | 1.0 | 36.7 | 10.1 | 18.9 | 1.0 | 3.6 | 0.4 |
| 0.80 | 0.4320 | 5.15 | 1.17 | 21.99 | 29.8 | 1.0 | 28.0 | 11.1 | 22.7 | 1.0 | 2.5 | 0.6 |
| 1.20 | 0.6480 | 4.78 | 1.00 | 20.78 | 25.4 | 1.0 | 35.1 | 8.8  | 24.2 | 1.0 | 4.0 | 0.5 |
| 1.60 | 0.8640 | 5.97 | 1.58 | 26.44 | 25.3 | 1.0 | 44.6 | 7.9  | 13.8 | 1.0 | 5.6 | 0.3 |
| 2.00 | 1.0800 | 7.08 | 2.65 | 33.09 | 24.8 | 1.0 | 43.7 | 9.9  | 14.3 | 1.0 | 4.4 | 0.4 |
| 4.00 | 2.1600 | 8.23 | 3.26 | 39.38 | 26.8 | 1.0 | 40.4 | 8.3  | 10.1 | 1.0 | 4.9 | 0.3 |

Degree of unsaturation $\Delta U = \dfrac{(18:1 + 18:2 + 18:3)}{(18:0 + 16:0)}$

We claim:

1. A cyclopropene fatty acid, Δ12 or Δ15 desaturates enzyme inhibitor of formula (I)

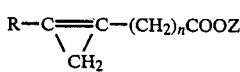

(I)

wherein R is a straight chain aliphatic group or 1 to 6 carbon atoms; n is an integer of from 10 to 15; and z is a hydrogen atom or an alkyl group of 1 to 6 carbon atoms.

2. A compound as claimed in claim 1 wherein R is a straight chain alkyl group of 1 to 5 carbon atoms.

3. A compound as claimed in claim 1 wherein n is an integer of from 10 to 14.

4. A compound as claimed in claim 1 wherein Z is either hydrogen or a methyl group.

5. A compound as claimed in claim 1 wherein n is 10.

6. A compound as claimed in claim 1 wherein n is 13.

7. A compound as claimed in claim 1 wherein the fatty acid is 17 or 18 carbon atoms long.

8. A compound as claimed in claim 1 which is a Δ12 desaturase enzyme inhibitor.

9. A compound as claimed in claim 1 which is a Δ15 desaturase enzyme inhibitor.

* * * * *